United States Patent [19]
Morgan et al.

[11] Patent Number: 5,480,974
[45] Date of Patent: Jan. 2, 1996

[54] ANTIBODIES TO HUMAN C5A RECEPTOR

[75] Inventors: Edward L. Morgan, San Diego; Julia A. Ember, Rancho Santa Fe; Tony E. Hugli, San Diego, all of Calif.

[73] Assignee: The Scripps Research Institute, La Jolla, Calif.

[21] Appl. No.: 79,051

[22] Filed: Jun. 18, 1993

[51] Int. Cl.$^6$ .............. C07K 15/28; C07K 15/00; C12N 5/12

[52] U.S. Cl. ............... 530/387.9; 530/388.25; 530/389.1; 530/389.3; 435/240.27

[58] Field of Search .............. 530/387.9, 389.1, 530/387.1, 388.25, 389.3; 435/240.27

[56] References Cited

PUBLICATIONS

Morgan, E. L. et al., J. Immunol, 151(1): 377–388, Jul. 1, 1993.
Oppermann, M. et al., Immunobiology, 186(1–2): 58, Oct. 28–31, 1992.
Gerard, N. P. et al, Nature, 349: 614–617, 14 Feb. 1991.
Embers, J. A. et al., J. Immunol, 148(10): 3165–3173, May 15, 1992.
Lerner, R. A., Nature, 299: 592–596, 1982.
Oppermann, M. et al., J. Immunol, 151(7): 3785–3794, Oct. 1, 1993.

*Primary Examiner*—David L. Lacey
*Assistant Examiner*—Susan A. Loring
*Attorney, Agent, or Firm*—Spensley Horn Jubas & Lubitz

[57] ABSTRACT

A peptide-specific monoclonal antibody derived from an immunogenic peptide from the extracellular hydrophilic region of the human C5 a receptor (C5aR) is useful for blocking C5a from binding to C5aR.

5 Claims, 12 Drawing Sheets

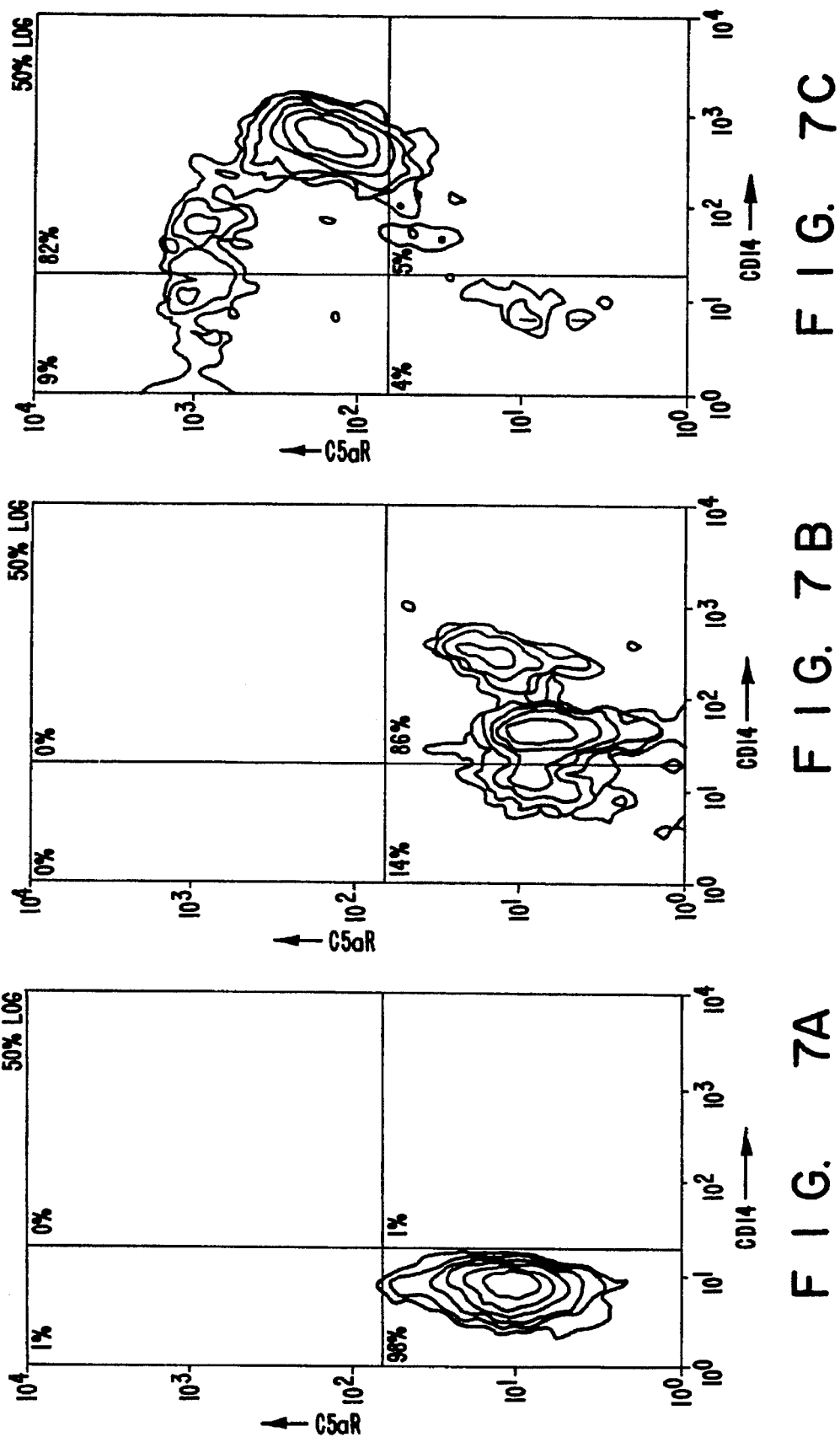

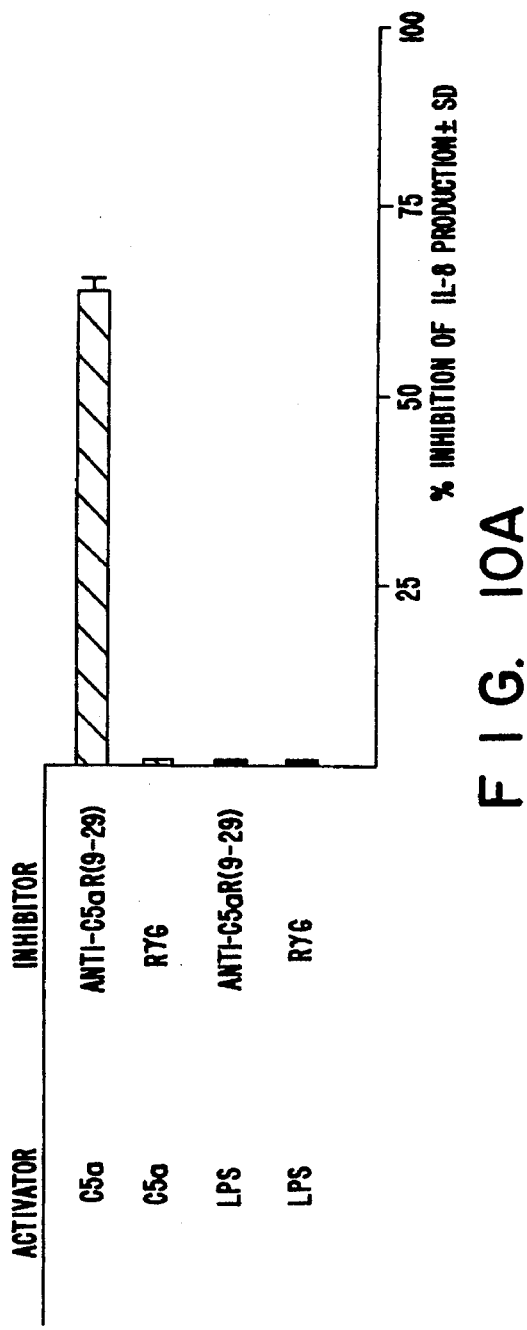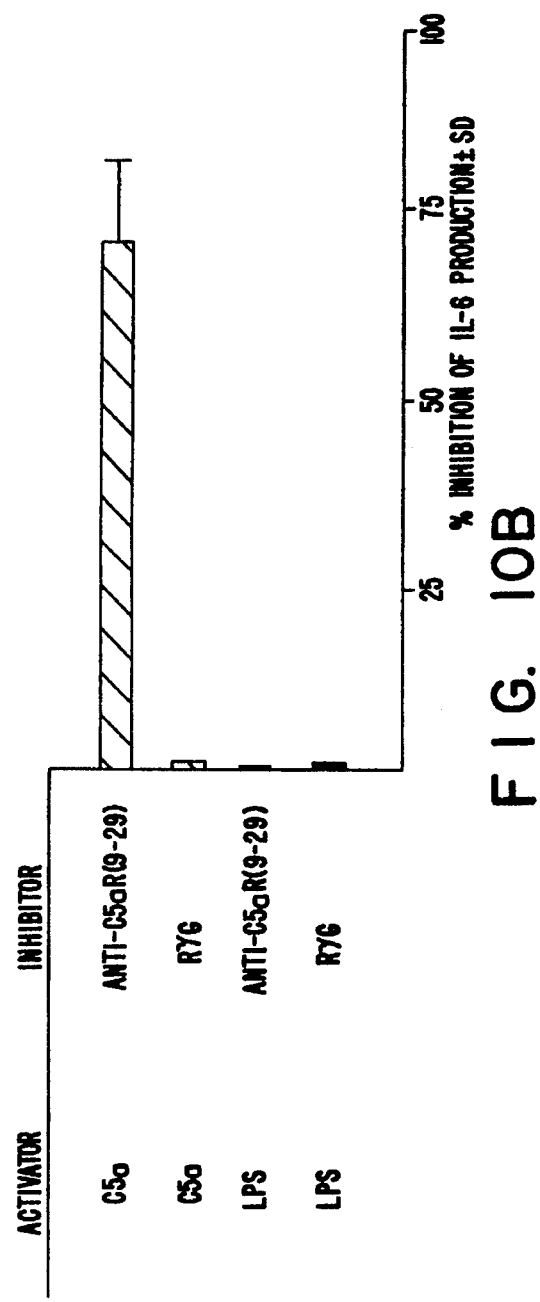

ANTIBODIES TO HUMAN C5A RECEPTOR

This invention was made with Government support under Grant Nos. AI 32503, AI 16411, HL 25658, and HL 16411, awarded by the National Institutes of Health. The Government has certain rights in this invention.

BACKGROUND OF THE INVENTION

1. Field of the Invention

This invention relates to the field of immunology and specifically to monoclonal antibodies which bind to a specific sequence within the C5a receptor.

2. Description of Related Art

In man, and in most animals, the complement system is composed of a group of proteins that are normally present in serum in an inactive state. When activated, these proteins participate in a coordinated series of reactions. Activation of the complement system results in enzymatic cleavage of complement proteins producing numerous subfragments which possess a wide range of biologic activities required for host defense, including the elimination of invading microorganisms. During an inflammatory process, local production of complement-derived mediators result in increased vascular permeability, leukocyte adherence to endothelial and vascular tissue, and a chemotactic gradient that induces neutrophil (PMN) migration into the inflammatory site. In addition to beneficial aspects of the inflammatory process, systemic and/or chronic inflammatory processes have been associated with a variety of immune disease states. C5a is one of the best described and most potent proinflammatory mediators derived from the complement system. C5a has been shown to be spasmogenic (Stimler, et al., *J. Immunol.* 126:2258, 1981), chemotactic (Hugli, et al., *Adv. Immunol.* 26:1, 1978), to increase vascular permeability (Shin, et al., *Science* 162:361, 1968), and to induce the release of pharmacologically active mediators from numerous cell types (Grant, et al., *J. Immunol.* 114:1101, 1975; Goldstein, et al., *J. Immunol.* 113:1583, 1973; Schorlemmer, et al., *Nature* 261:48, 1976). Most recently, C5a has been shown to directly or indirectly induce cytokine release from macrophages and to augment humoral- and cell-mediated immune responses in vitro. Combined, these studies indicate that C5a possesses multiple biologic activities important in host defense and may also play a role in inflammatory disease processes. Many cell types possess receptors for C5a, including PMNs, macrophages, mast cells and platelets.

Numerous antibodies directed to PMN surface determinants have been generated to study inflammatory mediator-cell interactions. The majority of these monoclonal or polyclonal antibodies have lacked specificity. Some have shown limited specificity, primarily those involving N-formyl chemotactic peptide (f-MLF)-receptor interactions. These antibodies to f-MLF have been shown to suppress or mimic ligand-induced chemotaxis, phagocytosis, adherence, exocytosis, enzyme release, or the oxidative burst. To date, generation of antibodies specific for the C5a receptor has proven to be problematic. Although the solubilization of a functional C5a receptor from human PMN has been achieved, attempts to purify sufficient quantities of C5a receptor to homogeneity for the production of antibodies has failed.

The availability of C5a receptor-specific neutralizing antibodies would provide not only an important Tool for dissecting the mechanisms of C5a-mediated cellular activation, but would also represent an important therapeutic reagent, useful in controlling inflammatory and autoimmune diseases. The present invention answers this need.

SUMMARY OF THE INVENTION

The present invention provides a 21 amino acid residue peptide found in the extracellular hydrophilic region of the human C5a receptor (C5aR) and an antibody which specifically binds to the peptide. This site-directed antibody specifically interacts with several cell types which express C5aR, blocks C5a-mediated PMN chemotaxis, inhibits C5a-mediated PMN enzyme release, and neutralizes C5a-mediated cytokine production by human macrophages.

The invention also provides a method of treating a subject having or at risk of having an immunopathological disorder associated with the peptide of the invention comprising administering to the subject an immunotherapeutically effective amount of the peptide or peptide-specific antibody to ameliorate the disorder.

BRIEF DESCRIPTION OF THE DRAWINGS

FIGS. 7A, B, and C show a two color flow cytometry analysis of human macrophages.

FIGS. 10A and B show the percent inhibition of IL-6 and IL-8 production from human macrophages by anti-C5aR (9–29).

DETAILED DESCRIPTION OF THE INVENTION

Figure 1:
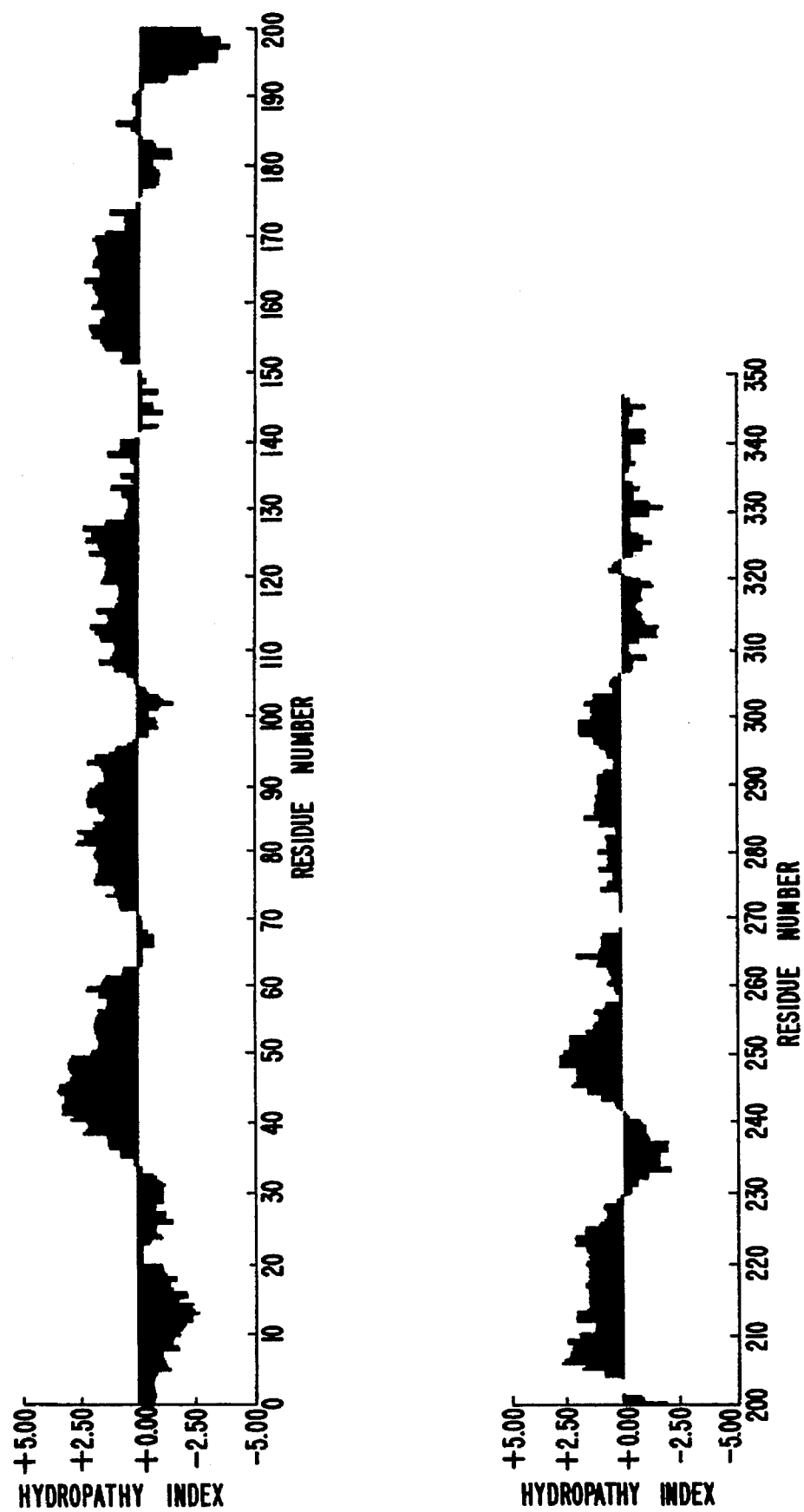
FIG. 1 is a hydropathy plot of the predicted residues of the human C5aR.

The present invention provides a unique synthetic immunogenic peptide which is derived from the C5a receptor (C5aR). Also included in the invention are antibodies which bind to the peptide. Both the peptide and the antibodies which bind the peptide are useful immunodiagnostically and immunotherapeutically to monitor and treat immunopathological disorders.

As used herein, the term "synthetic immunogenic peptide" denotes a peptide which does not comprise an entire naturally occuring protein molecule. These peptides are "synthetic" in that they may be produced by human intervention using such techniques as chemical synthesis, recombinant genetic techniques, or fragmentation of whole antigen or the like. "Immunogenic" means that the peptides of the invention can participate in an immune response. This participation can be, for example, either passive or active participation. Thus, the peptides can be passively utilized, for example, by interacting in vitro or in vivo with antibody which binds to an epitope located in the peptide. Alternatively, the peptides can be used actively, for example, to induce an immune response in a host.

The term "immunopathological disease" or "immunopathological disorder" refers to any disease which involves an immune response or immunity in general. Examples of immunopathological diseases include gram-negative bacterial sepsis, acute respiratory distress syndrome (ARDS), ischemic heart disease, post-dialysis syndrome, rheumatoid arthritis, acquired immune deficiency syndrome (AIDS) and vasculitis. Preferably, the immunopathological disorder is associated with the C5a and C5aR.

The peptide of the invention is about 21 amino acids and includes the amino acid sequence PDYGHYDDKDTLDLNTPVDKT (Sequence ID No. 1 ), which corresponds to amino acids 9–29 of the amino terminus of C5aR. The peptide may act as a competitive inhibitor with C5a, the natural ligand for C5aR. In addition, the peptide is immunogenic and therefore is useful for the production of antibodies which bind to the C5aR.

Minor modifications of the primary amino acid sequence of the peptide of the invention may result in peptides which have substantially equivalent activity as compared to the specific peptide described herein. Such modifications may be deliberate, as by site-directed mutagenesis, or may be spontaneous. All of the peptides produced by these modifications are included herein as long as the biological activity of the original peptide still exists. For example, a modified peptide must still competitively inhibit C5a and must be capable of participating in an immune response. Further, deletion of one or more amino acids can also result in a modification of the structure of the resultant molecule without significantly altering its biological activity. This can lead to the development of a smaller active molecule which would also have utility. For example, it is possible to remove amino or carboxy terminal amino acids which may not be required for biological activity of the particular peptide.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan, et al., *Current Protocols in Immunology*, Wiley Interscience, 1991, Unit 9). Peptides of the invention can also be synthesized by various well known solid phase peptide synthesis methods, such as those described by Merrifield, *J. Am. Chem. Soc.*, 85:2149, 1962), and Stewart and Young, *Solid Phase Peptides Synthesis*, (Freeman, San Francisco, 1969, pp.27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

The invention also provides polynucleotides which encode the peptides of the invention. As used herein, "polynucleotide" refers to a polymer of deoxyribonucleotides or ribonucleotides, in the form of a separate fragment or as a component of a larger construct. DNA encoding a peptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. A polynucleotide sequence can be deduced from the genetic code, however, the degeneracy of the code must be taken into account. Polynucleotides of the invention include sequences which are degenerate as a result of the genetic code.

Polynucleotide sequences encoding the peptides of the invention can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

In another aspect, the present invention is directed to polyclonal and monoclonal antibodies which bind to the peptide of the invention. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature*, 256: 495, 1975; *Current Protocols in Molecular Biology*, Ausubel, et al., ed., 1989).

The monoclonal antibodies of this invention can be biologically produced by introducing the peptide of the invention into a mouse or a rat. The antibody producing cells in the animal are isolated and fused with myeloma cells or heteromyeloma cells to produce hybrid cells or hybridomas. Accordingly, the hybridoma cells producing the monoclonal antibodies of this invention also are provided. Monoclonal antibodies produced in this manner include, but are not limited to the monoclonal antibodies produced by the hybridoma cell line designated 6G4. The hybridoma cell line 6G4 has been deposited with the American Type Culture Collection (ATCC) 12301 Parklawn Drive, Rockville, Md. 20852, U.S.A., under the provisions of the Budapest Treaty on the International Deposit of Microorganisms for the Purposes of Patent Procedure. This deposit was made on Jun. 14, 1993 and was accorded ATCC accession number ATCC HB 11384. The deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of deposit. The organisms will be made available by ATCC under the terms of the Budapest Treaty which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 C.F.R. § 1.14 with particular reference to 886 OG 638).

The assignee of the present application has agreed that if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cell lines deposited, since the deposited embodiment is intended as a single illustration of one aspect of the invention and any cell lines that are functionally equivalent are within the scope of this invention. The deposit of material does; not constitute an admission that the written description herein contained is inadequate to enable the practice of any aspect of the invention, including the best mode thereof, nor is it to be construed as limiting the scope of the claims to the specific illustration that it represents.

The term "antibody" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme: papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the peptide of the invention can be prepared using an intact polypeptide or fragments containing the peptides of interest as the immunizing antigen. A peptide used to immunize an animal can be derived from translated cDNA or chemical synthesis and is purified and conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse or a rabbit).

If desired, polyclonal antibodies can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference).

Methods known in the art allow antibody exhibiting binding for a preselected ligand to be identified and isolated from antibody expression libraries. For example, a method for the identification and isolation of an antibody binding domain which exhibits binding with a peptide of the invention is the bacterio-phage λ vector system. This vector system has been used to express a combinatorial library of Fab fragments from the mouse antibody repertoire in *Escherichia coil* (Huse. et al., *Science*, 246:1275–1281, 1989) and from the human antibody repertoire (Mullinax, et al., *Proc. Natl. Acad. Sci.*, 87:8095–8099, 1990). As described therein, antibody exhibiting binding for a preselected ligand were identified and isolated from these antibody expression libraries. This methodology can also be applied to hybridoma cell lines expressing monoclonal antibodies with binding for a preselected ligand. Hybridomas which secrete a desired monoclonal antibody can be produced in various ways using techniques well understood by those having ordinary skill in the art and will not be repeated here. Details of these techniques are described in such references as *Monoclonal Antibodies-Hybridomas: A New Dimension in Biological Analysis*, Edited by Roger H. Kennett, et al., Plenum Press, 1980; and U.S. Pat. No. 4,172,124, incorporated by reference.

In addition, methods of producing chimeric antibody molecules with various combinations of "humanized" antibodies are known in the art and include combining murine variable regions with human constant regions (Cabily, et al. *Proc. Natl. Acad. Sci. USA*, 81:3273, 1984), or by grafting the murine-antibody complementary determining regions (CDRs) onto the human framework (Riechmann, et al., *Nature* 332:323, 1988).

This invention further provides chimeric antibodies of the peptide-specific antibodies described above or biologically active fragments thereof. As used herein, the term "chimeric antibody" refers to an antibody in which the variable regions of antibodies derived from one species are combined with the constant regions of antibodies derived from a different species or alternatively refers to CDR grafted antibodies.

Chimeric antibodies are constructed by recombinant DNA technology, and are described in Shaw, et al., *J. Immun.*, 138:4534 (1987), Sun, L. K., et al., *Proc. Natl. Acad. Sci. USA*, 84:214–218 (1987), for example.

Any of the above described antibodies or biologically active antibody fragments can be used to generate CDR grafted and chimeric antibodies. "CDR" or "complementarity determining region" or "hypervariable region" is defined as the amino acid sequences on the light and heavy chains of an antibody which form the three-dimensional loop structure that contributes to the formation of the antigen binding site.

As used herein, the term "CDR grafted" antibody refers to an antibody having an amino acid sequence in which at least parts of one or more CDR sequences in the light and/or variable domain have been replaced by analogous parts of CDR sequences from an antibody having a different binding specificity for a given antigen or receptor.

The terms "light chain variable region" and "heavy chain variable region" refer to the regions or domains at the N-terminal portion of the light and heavy chains respectively which have a varied primary amino acid sequence for each antibody. The variable region of the antibody consists of the amino terminal domain of the light and heavy chains as they fold together to form a three-dimensional binding site for an antibody.

The analogous CDR sequences are said to be "grafted" onto the substrate or recipient antibody. The "donor" antibody is the antibody providing the CDR sequence, and the antibody receiving the substituted sequences is the "substrate" antibody. One of skill in the art can readily produce these CDR grafted antibodies using the teachings provided herein in combination with methods well known in the art (see Borrebaeck, C. A., *Antibody Engineering: A Practical Guide*, W. H. Freeman and Company, New York, 1992, incorporated by reference).

The monoclonal antibodies of the invention are immunoreactive and bind with the peptide of the invention. The monoclonal antibody 6G4 ATCC HB11384 binds to a peptide corresponding to amino acid residues 9–29 of the amino terminus of the C5a receptor (PDYGHYDDKDTLDLNTPVDKT (Sequence ID No.1)).

Under certain circumstances, monoclonal antibodies of one isotype might be more preferable than those of another in terms of their diagnostic or therapeutic efficacy. For example, from studies on antibody-mediated cytolysis it is known that unmodified mouse monoclonal antibodies of isotype gamma-2a and gamma-3 are generally more effective in lysing target cells than are antibodies of the gamma-1 isotype. This differential efficacy is thought to be due to the ability of the gamma-2a and gamma-3 isotypes to more actively participate in the cytolytic destruction of the target cells. Particular isotypes of a monoclonal antibody can be prepared secondarily, from a parental hybridoma secreting monoclonal antibody of different isotype, by using the sib selection technique to isolate class-switch variants (Steplewski, et al., *Proc. Natl. Acad. Sci. U.S.A.*, 82:8653, 1985; Spira, et al., *J. Immunol. Methods*, 74:307, 1984). Thus, the monoclonal antibodies of the invention would include class-switch variants having the specificity of monoclonal antibody which is produced by ATCC HB11384.

The invention also provides cell lines which produce monoclonal antibodies of the invention. The isolation of cell lines producing monoclonal antibodies of the invention can be accomplished using routine screening techniques which permit determination of the elementary reaction pattern of the monoclonal antibody of interest. Thus, if a monoclonal antibody being tested binds and neutralizes the activity associated with the specific peptide, for example binds C5aR and blocks C5a-mediated biological activity, then the monoclonal antibody being tested and the monoclonal antibody produced by the cell lines of the invention are equivalent.

It is also possible to determine, without undue experimentation, if a monoclonal antibody has the same specificity as a monoclonal antibody of the invention by ascertaining whether the former prevents the latter from binding to the peptide. If the monoclonal antibody being tested competes with the monoclonal antibody of the invention, as shown by a decrease in binding by the monoclonal antibody of the invention, then the two monoclonal antibodies bind to the same, or a closely related, epitope.

Still another way to determine whether a monoclonal antibody has the specificity of a monoclonal antibody of the invention is to pre-incubate the monoclonal antibody being tested with the peptide to which the antibody is presumed to be reactive, and then add the monoclonal antibody of the invention to determine if the monoclonal antibody of the invention is inhibited in its ability to bind the peptide. If the monoclonal antibody of the invention is inhibited then, in all likelihood, the monoclonal antibody being tested has the same, or functionally equivalent, epitopic specificity as the monoclonal antibody of the invention. Screening of monoclonal antibodies of the invention, can also be carried out utilizing the peptides and determining whether the monoclonal antibody blocks C5a from binding to C5aR.

By using the monoclonal antibodies of the invention, it is possible to produce anti-idiotypic antibodies which can be used to screen monoclonal antibodies to identify whether the antibody has the same binding specificity as a monoclonal antibody of the invention. These antibodies can also be used for immunization purposes (Herlyn, et al., *Science*, 232:100, 1986). Such anti-idiotypic antibodies can be produced using well-known hybridoma techniques (Kohler and Milstein, *Nature*, 256:495, 1975). An anti-idiotypic antibody is an antibody which recognizes unique determinants present on the monoclonal antibody produced by the cell line of interest. These determinants are located in the hypervariable region of the antibody. It is this region (paratope) which binds to a given epitope and, thus, is responsible for the specificity of the antibody. An anti-idiotypic antibody can be prepared by immunizing an animal with the monoclonal antibody of interest. The immunized animal will recognize and respond to the idiotypic determinants of the immunizing antibody and produce an antibody to these idiotypio determinants. By using the anti-idiotypic antibodies of the immunized animal, which are specific for a monoclonal antibody of the invention produced by a cell line which was used to immunize the second animal, it is now possible to identify other clones with the same idiotype as the antibody of the hybridoma used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, the anti-idiotypic monoclonal antibody can be used for immunization, since the anti-idiotype monoclonal antibody binding domain effectively acts as an antigen.

The monoclonal antibodies of the invention are suited for use in vitro, for example, in immunoassays in which they can be utilized in liquid phase or bound to a solid phase carrier. The antibodies may be useful for monitoring the level of C5aR in a sample. Similarly, anti-idiotype antibodies are useful for measuring the level of C5a in a sample. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of C5aR or polypeptides which contain a peptide of the invention. Examples of well-known carriers include glass, polystyrene, poypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

The monoclonal antibodies of the invention can also be used for in vivo diagnosis, such as to identify a site of infection or inflammation or to monitor a particular therapy. In using the monoclonal antibodies of the invention for the in vivo detection of antigen having a peptide of the invention, the detectably labeled monoclonal antibody is given in a dose which is diagnostically effective. The term "diagnostically effective" means that the amount of detectably labeled monoclonal antibody is administered in sufficient quantity to enable detection of the site having cells which express C5aR or other antigens for which the monoclonal antibodies bind by virtue of the presence of the particular peptide of the invention.

The concentration of detectably labeled monoclonal antibody which is administered should be sufficient such that the binding to a peptide of the invention is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.01 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tissue, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

The monoclonal antibodies of the invention can be used in vitro and in vivo to monitor the course of disease therapy. For purposes of the invention, the peptide of the invention may be used diagnostically in biological fluids and tissues to monitor the fate of monoclonal antibodies used therapeutically. Any sample containing a detectable amount of monoclonal antibody can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

The monoclonal antibodies can also be used immunotherapeutically for immunopathological associated disease. The term "immunotherapeutically" or "immunotherapy" as used herein in conjunction with the monoclonal antibodies of the invention denotes both prophylactic as well as therapeutic administration. Thus, the monoclonal antibodies can be administered to high-risk patients in order to lessen the likelihood and/or severity of immunopathological disease or administered to patients already evidencing active disease, for example sepsis due to gram-negative bacterial infection.

As used herein, the term "ameliorate" denotes a lessening of the detrimental effects of the C5a/C5aR associated immunopathological disorder in the subject receiving therapy. The term "therapeutically effective" means that the amount of monoclonal antibody or peptide used is of sufficient quantity to ameliorate the C5a/C5aR associated immunopathological disorder.

An immunotherapeutic method in accordance with this invention entails the administration of a therapeutic agent of the invention by injection or infusion prior to (prophylaxis) or following (therapy) the onset of the immunopathological disease. The therapeutic agent may be a monoclonal antibody of the invention which binds to a peptide of the invention. Alternatively, the therapeutic agent may be a peptide of the invention. In addition, an anti-idiotype antibody which binds to a monoclonal antibody which binds a peptide of the invention may also be used in the immunotherapeutic method of the invention. All three types of therapeutic agents share the common trait of being able to inhibit the interaction of C5a with C5aR. The amount of therapeutic agent required to inhibit binding of an antigen to a cell receptor (e.g., C5aR) or to bind directly to the causative antigen (e.g., anti-idiotype antibodies binding to C5a) to inhibit its biological effects depends on such factors as the type and severity of the infection, the size and weight of the infected subject, and the effectiveness of other concomitantly employed modes of prophylaxis or therapy. These parameters are easily evaluated by those of ordinary skill in the art such that appropriate dosages can be established without undue experimentation.

The immunotherapeutic method of the invention includes a prophylactic method directed to those humans at risk for immunopathological diseases associated with C5a/C5aR interaction. A peptide of the invention can be administered to a host to induce an active immune response to the peptide, for example, such that the the host produces antibody to the peptide which inhibits or ameliorates the pathologic effect associated with a polypeptide (e.g., C5aR) having the peptide sequence of the invention. A prophylactically effective amount of a pharmaceutical composition containing a peptide or antibody of the invention is administered to the patient in an amount which is capable of blocking C5a from binding to a cell receptor (e.g., C5aR) which has the peptide sequence of the invention. Alternatively, a pharmaceutical composition containing antiidiotype antibodies which are capable of binding to the causative antigen (e.g., C5a) to prevent binding to a receptor, thereby neutralizing its biological activity.

The dosage ranges for the administration of the monoclonal antibodies of the invention are those large enough to produce the desired effect in which the symptoms of the immunopathological disease are ameliorated or the likelihood of infection or over stimulation of the immune system decreased. The dosage should not be so large as to cause adverse side effects, such as hyper-viscosity syndromes, pulmonary edema, conjestive heart failure, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

The monoclonal antibodies of the invention can be administered parenterally by injection or by gradual infusion over time. The monoclonal antibodies of the invention can be administered intravenously, intraperitoneally, intramuscularly, subcutaneously, intracavity, or transdermally.

The peptide of the invention can be administered by methods described for administration of the monoclonal antibodies. Preferred methods for delivery of the peptide include orally, by encapsulation in microspheres or proteinolds, by aerosol delivery to the lungs, or transdermally by iontophoresis or transdermal electroporation. Other methods of administration will be known to those skilled in the art.

Preparations for parenteral administration of a peptide or an antibody of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Using the monoclonal antibodies in the therapeutic method of the invention, it is possible to design therapies combining all of the characteristics described herein. For example, in a given situation, it may be desirable to administer a therapeutic agent, or agents, prior to the administration of the monoclonal antibodies or peptide of the invention.

The following examples; are intended to illustrate but not limit the invention. While they are typical of those that might be used, other procedures known to those skilled in the art may alternatively be used.

EXAMPLE 1

MATERIALS AND METHODS

1. Preparation of Human Cells
a. PBMC
Venous blood was collected, in heparin, from healthy adults of both sexes who donated through the General Clinical Research Center, Scripps Research Institute (La Jolla, Calif.). The peripheral blood-derived mononuclear cells (PBMC) were isolated by Ficoll-Hypaque (Pharmacia Fine Chemicals, Piscataway, N.J.) density gradient centrifugation.
b. PMN
PMN were isolated from EDTA treated venous blood by gravity sedimentation in 6% dextran followed by Ficoll-Hypaque density gradient centrifugation. The purified PMN fraction contained 95–98% PMN and 2–5% mononuclear cells as determined by Turk staining.
2. Reagents
Natural human C5a and C3a were prepared according to established procedures (Hugli, et al., *Mol. Cell. Biochem.* 41:59, 1981). f-MLF was obtained from Sigma. Chemical Co. (St. Louis, Mo.).
3. Antisera
Alkaline phosphatase (AP)-conjugated goat F(ab')$_2$ anti-rabbit IgG (H+L) was obtained from Tago Inc. (Burlingame, Calif.). The following Abs were used for flow cytometry analysis: phycoerythrin(PE)-conjugated donkey F(ab')$_2$ anti-rabbit IgG (H+L) (Jackson Immunoresearch, West Grove, Pa.); fluorescein (FITC)-conjugated monoclonal anti-CD14 (Dako Corp., Carpinteria, Calif.). All reagents were used according to manufacturer's directions.
4. Synthesis of C5aR-Derived Analogue Peptides
a. Peptide Synthesis
Peptides were synthesized according to the general principles of solid phase methodology with the assistance of an Applied Biosystems (Foster City, Calif.) Model 430A peptide synthesizer. The structure of C5aR peptides are as follows: C5aR(9–29) KAPDYGHYDDKDTLDLNTPVDKT (Sequence ID No. 1 ) and C5aR(133–148) KARFLLVEFKPIWCQNFR (Sequence ID No. 2). All syntheses were performed on a 0.25 mmol scale using p-hydroxymethylphenoxymethyl polystyrene (HMP) resin as the solid phase support (0.88 mmol/g substitution). Nα-amino groups were protected throughout the synthesis with the base label 9-fluorenylmethyloxycarbonyl (Fmoc) group. Side chain functional groups were protected as follows: Arg (Pmn or 2,2,5,7,8-pentamethyl-chroman-6-sulfonyl); Asp and Glu (OtBu or tert-butyl ester); His (Trt or trityl); Lys (boc or tertbutyloxycarbonyl); Ser, Thr, Tyr (tBu or tert-butyl). Peptide synthesis was initiated by the in situ double coupling of the C-terminal residue (Nα-Fmoc-L-Arg(Pmc)) to the HMP resin in the presence of excess N-N'dicyclohexylcarbodiimide (DCC) and 1-hydroxybenzotriazole (HOBT) along with 4-dimethylaminopyridine (DMAP) as a coupling catalyst. Peptide chain elongation was accomplished by repetitive Fmoc deprotection immediately followed by residue coupling via the preformed HOBT ester.

b. Deprotection and Cleavage

Side chain deprotection and resin cleavage was achieved simultaneously in a single step acidolysis reaction by stirring resin in a solution of 84% trifluoroacetic acid (TFA), 6% phenol, 2% ethanedithiol, 4% thioanisole, and 4% water for 1.5 h at room temperature. Free peptide was precipitated from this solution by adding excess cold diethyl ether. The mixture was filtered through a scintered glass buchner funnel (medium porosity) and the peptide/resin was washed twice with cold diethyl ether to remove the thiol scavengers. The peptide was extracted by swirling the peptide/resin in the scintered glass funnel with 20–30 ml aliquots of 10% acetic acid followed by filtration. The extraction aliquots were combined, frozen, and lyophilized to yield the powder form of the crude peptide.

c. Peptide Purification

All peptides were purified by preparative and analytical reverse phase high performance liquid chromatography (RP-HPLC) on columns packed with C18-bonded silica. The details of this purification procedure have been described in detail elsewhere (Ember, J. A., et al., *J. Immunol.*, 148:3165, 1992). All peptides were characterized by amino acid compositional analysis and fast atom bombardment mass spectrometry (FAB-MS).

5. Cell Culture Conditions

PBMC Cytokine Synthesis

PBMC were suspended in serum free medium consisting of KC 2000 (Hazelton, Lenexa, KS) supplemented with 1 mM pyruvate and 25 μg gentamicin/ml (M. A. Bioproducts). For the induction of IL-6 and IL-8 synthesis, $5 \times 10^6$ cells/ml were cultured in 12×75 mm round bottom culture tubes (Falcon Plastics, Becton Dickenson, Oxnard, Calif.) for 18–24 h. Culture supernatants were collected and stored at −20° C. until assayed for the presence of cytokines by ELISA. For cytokine synthesis-inhibition experiments, $5 \times 10^6$ cells/ml were preincubated for 1.5 h with $F(ab')_2$ fragments of specific Ab or normal rabbit gamma-globulin RγG. Following preincubation, activators were added and the supernatants were collected after 18–24 h. The following formula was used to calculate the degree of anti-C5aR(9–29)-induced inhibition of cytokine production:

$$\% \text{ Suppression} = \left(1 - \frac{\text{cytokine release in } Ab \text{ treated cultures}}{\text{cytokine release in control cultures}}\right) \times 100$$

6. Measurement of Cytokine Synthesis

IL-6 and IL-8 concentrations in PBMC culture-supernatants were determined by ELISA (R&D) Systems, Minneapolis Minn.) according to the manufacturer's instructions.

a. PMN Cherootaxis

Chemotaxis of human PMNs was measured as described previously (Ember, J. A., et al. *J. Immunol.*, .148:3165, 1992) in modified Boyden chambers (Adaps Inc., Dedham, Mass. - Model P1 & ½ SC). Cells migrating through the entire thickness of 8 μ micropore nitrocellulose filters (Sartorious, Gottingen, Germany), that separate the upper and lower chambers, were counted. Purified PMN suspended in 1% BSA-containing EBSS ($5 \times 10^6$ cells/ml) were placed in the upper chamber. PMNs were preincubated with different quantities of F(ab')2 anti-C5aR(9–29), $F(ab')_2$ RγG, or buffer control for 20 min. at room temperature for the chemotaxis-inhibition experiments. The lower chamber contained the chemoattractant [10% zymosan-activated human serum (ZAS) or f-MLF $(1–10^{-8}M)$] diluted in the same buffer. The number of migrated cells, following an incubation period of 90 min at 37° C. in 5% $CO_2$, was determined in samples taken from the lower chamber using a Sysmex Microcellcounter Model F-300. During the 90 min. incubation, a total of 40–60% of the untreated (control) cells migrated through the filter when 10% ZAS or f-MLF was added to the lower chamber. The buffer control induced between 1.5 and 5% of the cells to migrate. The following formula was used for calculating the degree of anti-C5aR(9–29) Ab-induced inhibition of cellular migration:

$$\% \text{ Suppression} = \left(1 - \frac{\text{No. of } Ab \text{ pre-incubated cells migrating}}{\text{No. of control cells migrating}}\right) \times 100$$

b. PMN Enzyme Release

The release of β-glucuronidase (β-G) from human PMNs was determined as described by Schroder, et al. *J. Immunol.*, 139:3474, 1987. Briefly, PMNs were treated with cytochalasin B (5 μg/ml for 10 min, 37° C.) followed by preincubation with or without F(ab')2 anti-C5aR(9–29) for 20 min at room temperature. A total of $1 \times 10^6$ cells were then incubated in the presence of stimulant ($1 \times 10^{-6}$M C5a or f-MLF) for 60 min at 37° C. in a final volume of 200 μl, and then centrifuged. Fifty μl of the culture supernatants were incubated with an equal volume of 0.01M p-nitrophenyl-β-D-glucuronide for 18 hr in microtiter wells. The reaction was stopped by the addition of 0.4M glycine buffer and the O.D. of triplicate samples was read at 405 nm. The β-G released was expressed as the percentage of total enzyme content of cell released by treatment with 0.2% Triton X-100. Inhibition of enzyme release by Ab-treatment of the cells was calculated by using the following formula:

$$\% \text{ Suppression} = \left(1 - \frac{\text{enzyme release in } Ab \text{ pretreated cells}}{\text{enzyme release in control cells}}\right) \times 100$$

7. Cloning and Expression of the Human C5a Receptor

Human HL-60 cells were differentiated into granulocytes with dibutryl cAMP (500 μM for 46 h) and mRNA was prepared from these cells. Double-stranded cDNA was synthesized and used as the template for PCR amplification of the human C5aR coding sequences. A pair of oligonucleotide primers (5' TAGAATTCCCAGCCAT-GAACTCCTTCAATTATACC-3' (SEQUENCE ID No. 3) and 5'-ACGAATTCTTACT-ACACTGC-CTGGGTCTTC- 3'(Sequence ID No. 4) were synthesized based on the published C5aR sequence (Gerard, N. P., et al. *Nature*, 349:61 4, 1991 ). After 30 cycles the PCR product was subcloned and sequenced. The sequence matched the published cDNA sequence for human C5aR. The PCR product was subcloned into the EcoR1 site of the expression vector SFFV.neo (Fuhlbrigge, R. C., et al., *Proc. Nat. Acad. Sci., USA*, 85:5649, 1988). The resulting plasmid (C5aR.neo) contained the coding sequence of C5aR cDNA downstream from the splenic focus-forming virus 5' long terminal repeat. Mouse L cell fibroblasts (ATCC CCL 1.1) were transfected with 20 μg of the linearized DNA, using the calcium phosphate method (Sambrook, J., et al., *Molecular Cloning: A Laboratory Manual. Cold Spring Harbor Laboratory Press*, Cold Spring Harbor, N.Y., 1989). Stable transfectants were selected by their ability to grow in concentrations of the antibiotic G 148 that is normally lethal to nontransfected cells. Approximately 50 positive transfectants were pooled for analysis.

8. PCR Analysis a. RNA Preparation.

Total RNA was isolated from $2 \times 10^6$ C5aR.neo transfected or untransfected L cells (ATCC CCL 1.1) cells or $1 \times 10^6$ HepG2 cells by a modified guanidine isothiocyanate/acid-phenol method described by Chomezynski, et al., (*Anal. Biochem.*, 162:156, 1987) using an RNA isolation kit (Stratagene, La Jolla, Calif.). To facilitate RNA precipitation, 20 μg of glycogen (Stratagene) was added to each tube. The amount of RNA was determined spectrophotometrically by measuring absorbance at 260 nm.

b. cDNA Library Construction.

Total RNA (5 μg) was reverse transcribed with MMLV reverse transcriptase (200 U/assay) and oligo (dT)12–18 (Gibco, Grand Island, N.Y.) as per manufacturer's instructions.

c. RT-PCR

RT-PCR was carried out in a 50 μl final volume containing; 5 μl 10x Taq reaction buffer, 33.4 μl ddH$_2$0, 0.4 μl mM dNTP's, 0.2 μl Taq polymerase (5 U/ml), 2 μl each (1 μM final concentration) of the 5' sense and 3'antisense primers for β-actin or the C5aR, and 10 μl of 1:10 diluted cDNA. All reagents for the RT-PCR reactions were obtained from Stratagene. After an initial incubation at 94° C. for 5 min. (denaturation) followed by 60° C. for 5 min (annealing) PCR was conducted in a thermal cycler for 35 cycles under the following conditions: 45 s denaturation at 94° C., 45 s annealing at 60° C., and 1.5 min extension at 72° C. The amplified DNA size was 249 bp for β-actin and 500 bp for human C5aR. Following amplification, the PCR fragments were analyzed by 3% agarose-gel electrophoresis and visualized by ethidium bromide staining.

9. Computer Analysis

The Protein Predictor software (for the Macintosh) for analysis of secondary structure (Atlantis Software, Wenham, Mass.) was used for hydropathy analysis. The pared t-Test for two treatment groups was used to analyze the data from multiple experiments. This was performed with the StatView 512 program (Brainpower Inc., Calabasas, Calif.). Unless otherwise stated, each experiment was performed a minimum of two times with different peripheral blood donors.

EXAMPLE 2

PRODUCTION AND CHARACTERIZATION OF ANTI-C5aR PEPTIDE ANTISERUM

Receptors for C5a have been described on many mammalian cells including PMN, macrophage-like cell lines. The human C5aR has recently been cloned from expression libraries prepared from mRNA derived from activated HL-60 and U937 cells (Gerard, supra; Boulay, et al., *Biochem.* 30:2993, 1991 ). These studies revealed a deduced protein sequence that contains 350 amino acid residues, giving a calculated molecular weight of 39,320. Structural analysis of the deduced sequence suggested that this protein shared features with members of the rhodopsin family including seven hydrophobic regions that presumably span the sell membrane (Gerard, et al., supra; Boulay, et al., supra; Dohlman, et al., *Ann. Rev. Biochem.* 60:653, 1991). Based on these predictions, the first 50 amino acid residues of the C5aR were subjected to hydropathy analysis (Kyte, J. et al., *J. Mol. Biol.* 157:105, 1982) to determine potential hydrophilic regions of the molecule. The results shown in FIG. 1 indicated that the N-terminal region of the molecule is relatively hydrophilic and could be exposed to the surface of the membrane. A 21 residue sequence was chosen from this region [C5aR(9–29)] (FIG. 1) and used to raise a specific polyclonal antibody (Ab).

The C5aR peptides were synthesized with lysine (K) and alanine (A) residues at the N-terminus of the molecules. K was added to facilitate conjugation to the carrier protein and A was added as a spacer residue. The C5aR peptide [C5aR(9–29)] was conjugated to keyhole limpet hemocyanin (KLH) with glutaraldehyde according to established procedures (Ahearn, J. M., et al., *Adv. Immunol.*, 46:183, 1989). 500 μg of the peptide-KLH conjugate in complete Freund's adjuvant (GIBCO, Grand Island, N.Y.) was administered subcutaneously in rabbits on day 0 followed by booster injections on days 30 and 60 in incomplete Freund's adjuvant. Serum was collected starting 75 days after the initial immunization.

Serum from rabbits immunized with C5aR(9–29) and normal rabbit serum were assessed for an ability to bind to plate-bound C5aR(9–29) and normal rabbit serum were assessed for an ability to bind to plate-bound C5aR(9–29) in an ELISA. The results shown in FIG. 2A indicate that serum from rabbits immunized with carrier conjugated-C5aR(9–29) binds free peptide in a dose-dependent manner with an ED$_{50}$ titer of approximately 1:20,000. In contrast, normal rabbit serum failed to bind to the peptide above background levels. Anti-C5aR Ab and normal rabbit γ-globulin (RγG) were purified by protein A Sepharose chromatography (Sigma) (Current Protocols in Immunology, Coligan, J. E., et al., Vol 1 J. Wiley and Co., N.Y., 1991) and the column eluates were assayed for peptide-specific Ab). F(ab')$_2$ fragments of the protein A purified specific Ab arid RγG were prepared by pepsin digestion according to established procedures (Coligan, et al., supra).

Figure 2A:
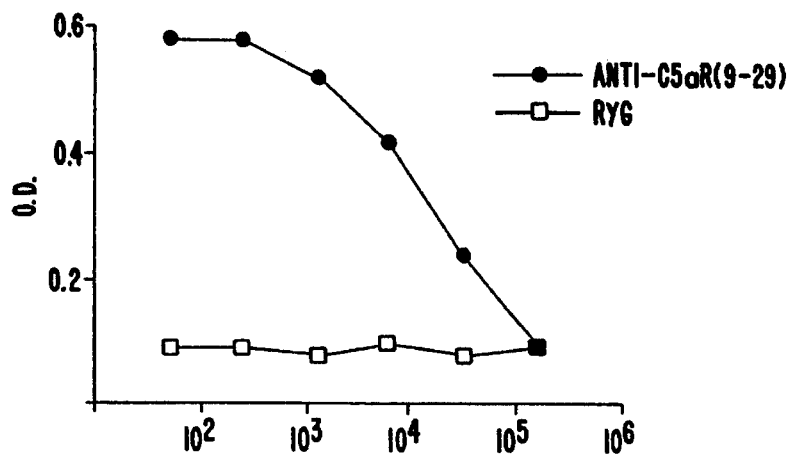
FIGS. 2A, B, and C show characterization of the rabbit anti-C5aR (9–29) antiserum.
Figure 2B:
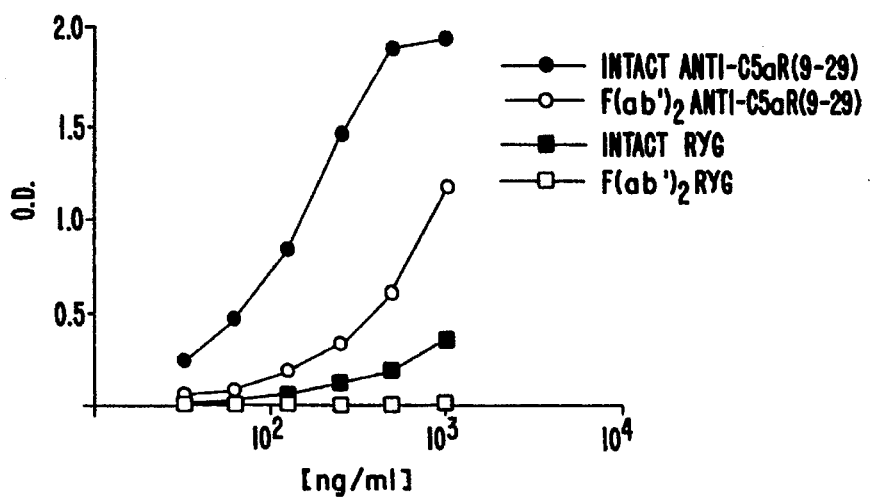
Figure 2C:
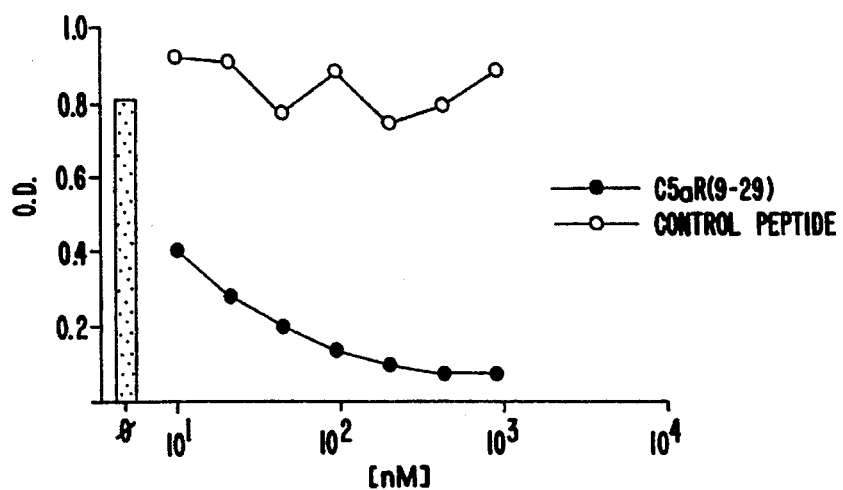

The results shown in FIG. 2B indicate that protein A purified Ab derived from immunized rabbits recognized C5aR(9–29). Normal RγG failed to bind to C5aR(9–29) in the peptide ELISA. FIGS. 2A, B and C show the characterization of the rabbit anti-C5aR(9–29) antiserum in the peptide specific ELISA. FIG. 2A-Dilutions of whole serum from immunized rabbits or control rabbits were tested for their ability to bind plate bound C5a(9–29); FIG. 2B protein A-purified anti-C5aR(9–29), RTG, and F(ab')2 fragments were treated for their ability to bind plate bound C5aR(9–29); FIG. 2C A constant amount of protein A-purified intact anti-C5aR(9–29) (100 ng/ml) was preincubated for 1 hr with increasing amount of C5aR(9–29) or control peptide and assessed for the ability to bind plate bound C5aR(9–29) in the ELISA.

In addition, F(ab')$_2$ fragments from both anti-C5aR(9–29) Ab and normal RγG were prepared and assayed for binding activity in the peptide ELISA. F(ab')$_2$ fragments of peptide-specific Ab retained binding activity albeit at a reduced level compared to intact Ab. Finally, to assess anti-peptide specificity, a constant amount of anti-C5aR(9–29) was preincubated with increasing quantities of free C5aR(9–29) or control peptide [C5aR(133–148)] for 1 h prior to testing in the peptide ELISA. The results presented in FIG. 2C indicate that free C5aR(9–29), but not control peptide, inhibited anti-C5aR binding to plate-bound C5aR(9–29) in a dose-dependent manner. Taken together, these results indicate that rabbits immunized with C5aR(9–29) produced antigen-specific high titer Ab.

EXAMPLE 3

BINDING OF ANTI-C5aR(9–29) AB TO CELLS EXPRESSING THE C5aR

To determine if the polyclonal anti-C5aR(9–29) antiserum could bind to cells expressing the intact human C5aR, mouse L cell transfectants expressing the human C5aR were constructed.

Figure 3:
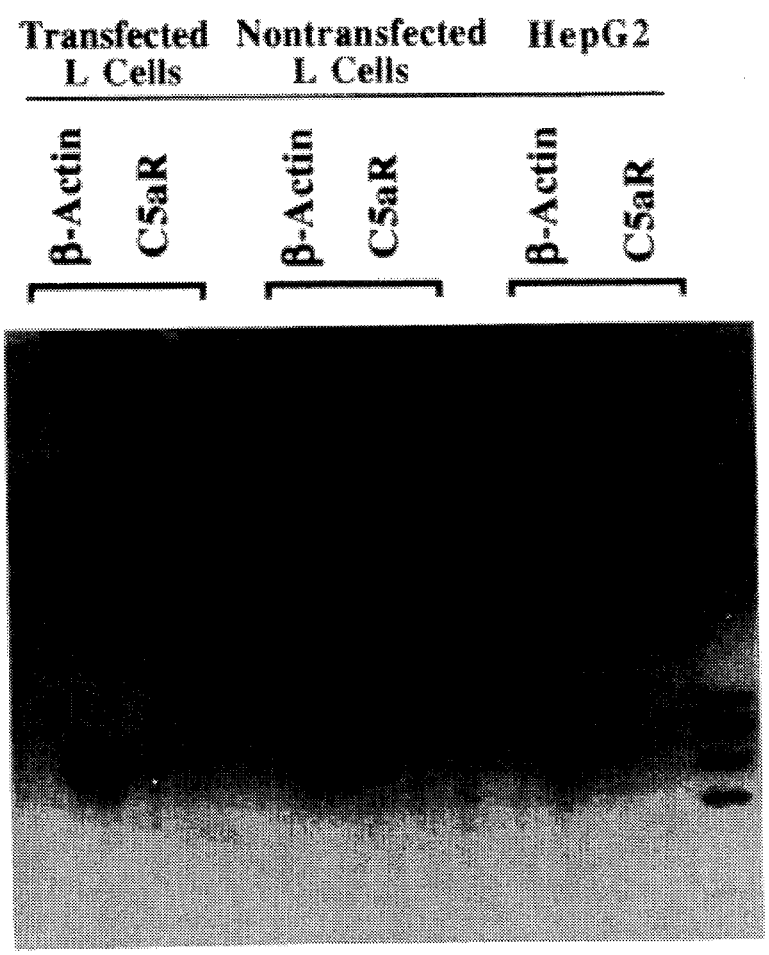
FIG. 3 shows a PCR analysis for expression of C5aR in transfected and nontransfected L-cells.

FIG. 3 shows the expression of human C5aR specific mRNA in C5aR.neo transfected or nontransfected murine L cells. First strand cDNA was prepared from total RNA isolated from transfected L cells, nontransfected L cells and HepG2 cells and subjected to RT-PCR analysis using 5' sense and 3' antisense primers specific for human C5aR and β-actin. The amplified DNA size was 500 bp for human C5aR and 249 bp for β-actin.

The results shown in FIG. 3 indicate that mouse L cells transfected with the C5aR.neo plasmid contained mRNA specific for the C5aR. In contrast, nontransfected L cells were negative for C5aR specific mRNA. The HepG2 cell line (known to express C5aR specific mRNA) was included as a positive control. Based on these results, protein A-purified anti-C5aR(9–29) and RγG were assessed for their ability to bind to L cells expressing the human C5aR.

Figure 4A:
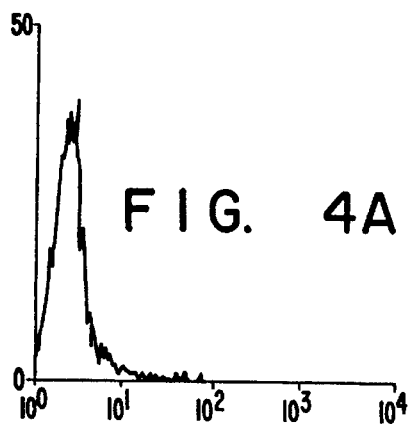
FIGS. 4A–F show a single color flow cytometry analysis of C5a.neo transfected and nontransfected murine L cells.
Figure 4B:
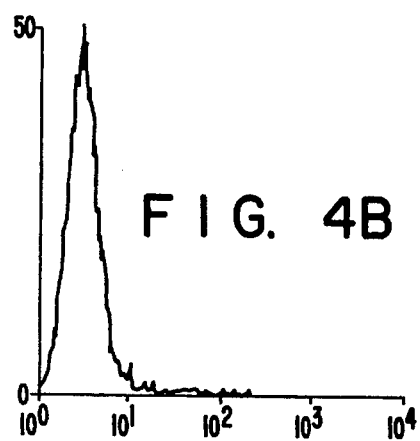
Figure 4C:
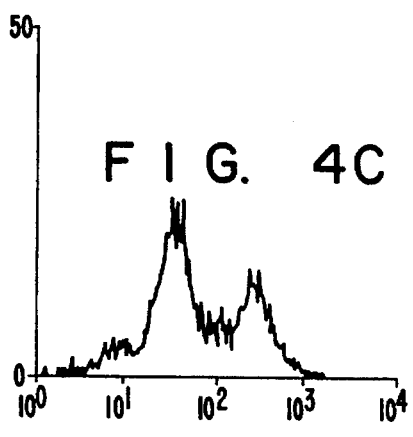
Figure 4D:
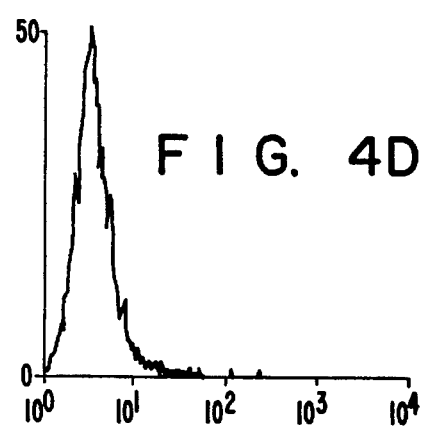
Figure 4E:
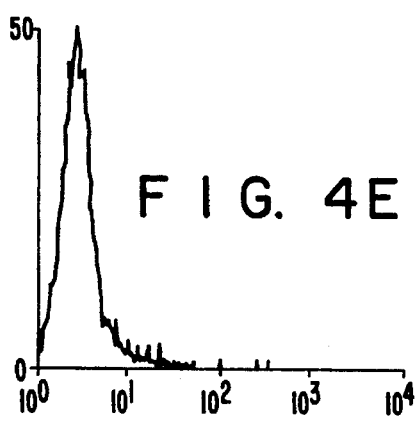
Figure 4F:
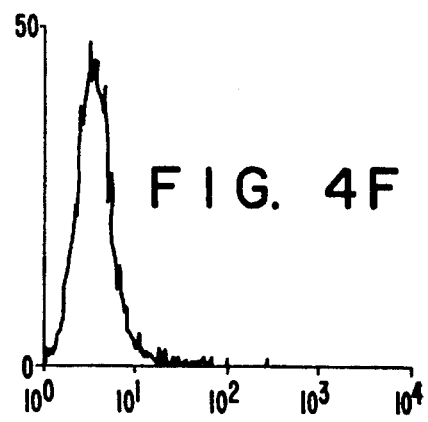

Single color flow cytometric analysis was performed as follows. 1×10$^6$ cells in staining buffer (PBS containing 1% FBS and 0.1% sodium azide) were incubated with anti-C5aR(9–29) or RγG for 30 min at 4° C., washed, and labeled with PE conjugated donkey (Fab')2 anti-rabbitt IgG for 30 min at 4° C. For dual color analysis FITC conjugated anti-CD14 was also included in the second incubation step. 1×10$^4$ cells were analyzed on a FACScan (Becton Dickinson, Mountain View, Calif.) and data analyzed with the LYSIS II software. For characterization of the macrophage containing population, forward and side scatter gates were set to include large granular cells. The results revealed that anti-C5aR(9–29) bound to L cells expressing the human C5aR with a greater mean fluorescence intensity (MFI) than to nontransfected L cells (FIG. 4 C and D). In addition, the results presented in FIG. 4C suggest that the C5aR.neo transfected cells are composed of at least two staining populations. This could be accounted for by the fact approximately 50 positive transfectants were pooled. Experiments are currently in progress to separate the two populations. In contrast, both transfected and nontransfected L cells bound RγG with a similar MFI (FIG. 4E and F). Based on these results, experiments were performed to determine if C5a could compete with anti-C5aR(9–29) for binding to C5aR.neo transfectants.

The transfected cells were preincubated with various quantities of human C5a or C3a, followed by addition of a constant amount of anti-C5aR(9–29) and suppression of Ab binding was measured in the cellular ELISA. The cellular ELISA was done according to published procedures (Coligan, et al., supra). Briefly, 1×10$^5$ C5aR.neo transfected L cells were preincubated, in staining buffer, with various amounts of human C5a, C3a, or buffer control for 1.5 hr at room temp. in V well microtiter plates (Linbro, Flow Laboratories, McLean, Va.). Following the preincubation, 7.5 µg/ml anti-C5aR(9–29) were added and the plates were incubated for 2 hr. at room temperature. The reaction was then developed with AP-conjugated F(ab')2 anti-rabbit IgG and substrate.

Figure 5:
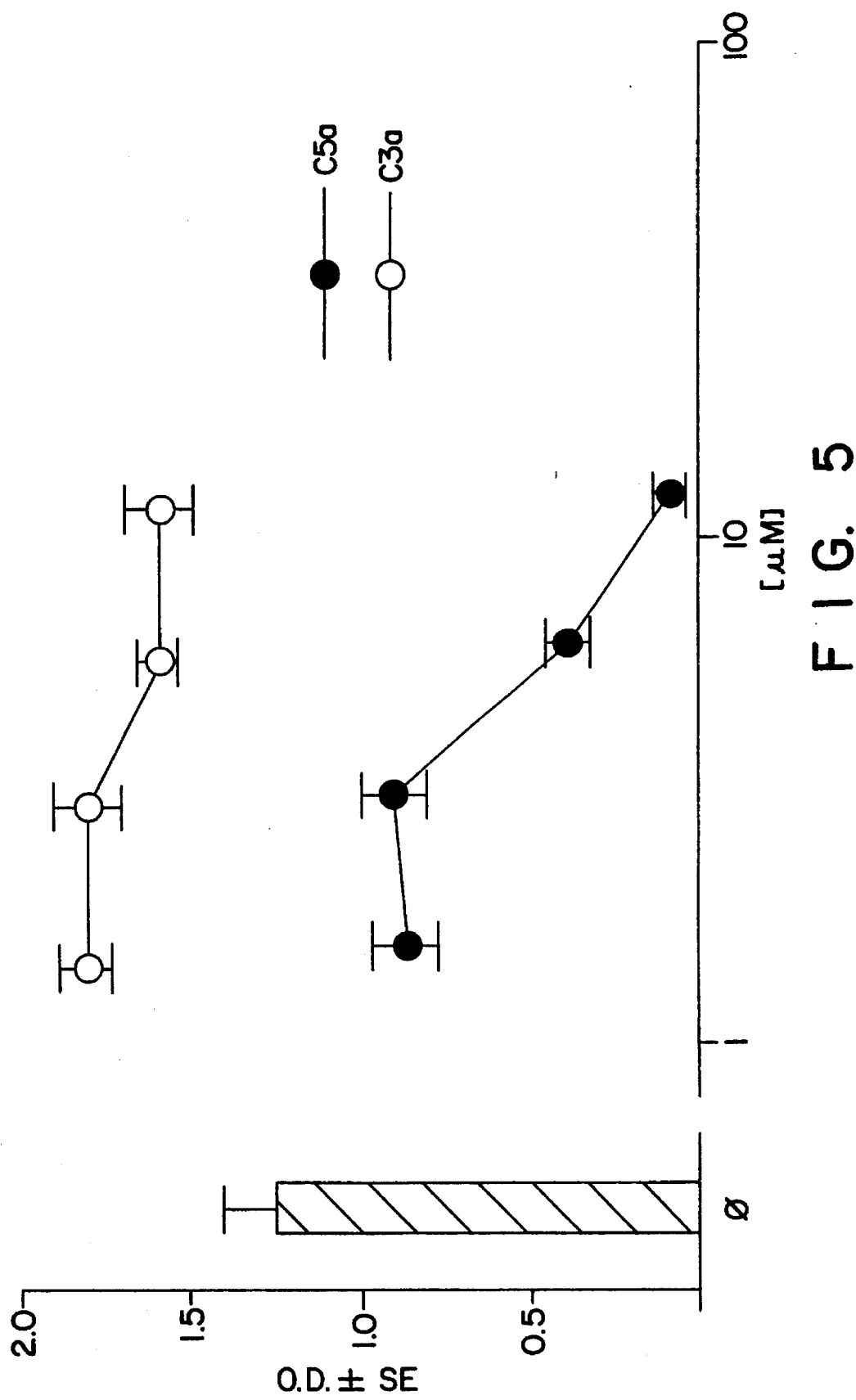
FIG. 5 shows the specific inhibition of anti-C5aR (9–29) binding to cells expressing the human C5aR.

FIG. 5 shows the inhibition of anti-C5aR(9–29) binding to cells expressing the human C5aR. C5a.neo transfected L cells were preincubated with staining buffer or increasing amount of human C5a or C3a for 1 h at room temperature. Following the preincubation of constant amount of protein A-purified intact anti-C 5aR(9–29)(7.5 µg/ml) was added and binding assessed in the cellular ELISA with the use of AP-conjugated F(ab')2 goat anti-rabbit IgG. Each data point represents the mean ± SE of 6 replicate wells.

The results shown in FIG. 5 indicate that natural C5a suppressed, in a dose dependent manner, the ability of anti-C5aR(9–29) to bind to cells expressing the C5aR. In contrast, tile C3a control failed to inhibit specific Ab binding to the cell population. The enhanced activity observed in the C3a preincubated wells could be accounted for by the fact that C3a is a highly charged molecule. These results suggest that the anti-C5aR peptide Ab directly interacts with the C5aR on transfected cells.

Figure 6A:
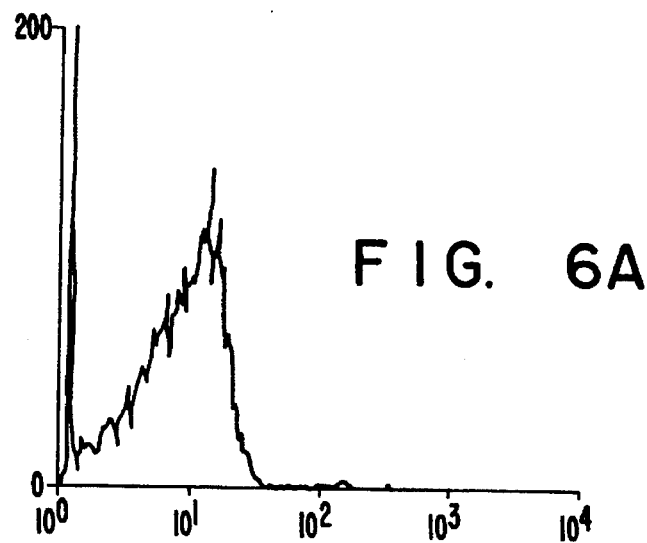
FIGS. 6A, B, and C show a single color flow cytometry analysis of normal human PMNs.
Figure 6B:
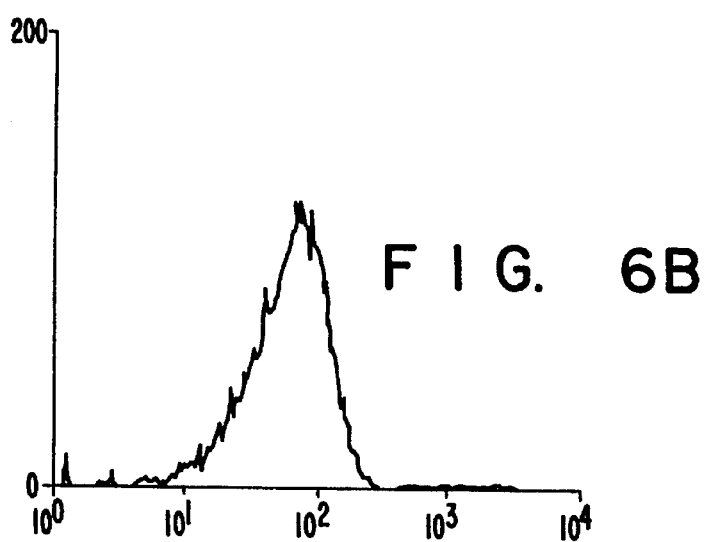
Figure 6C:
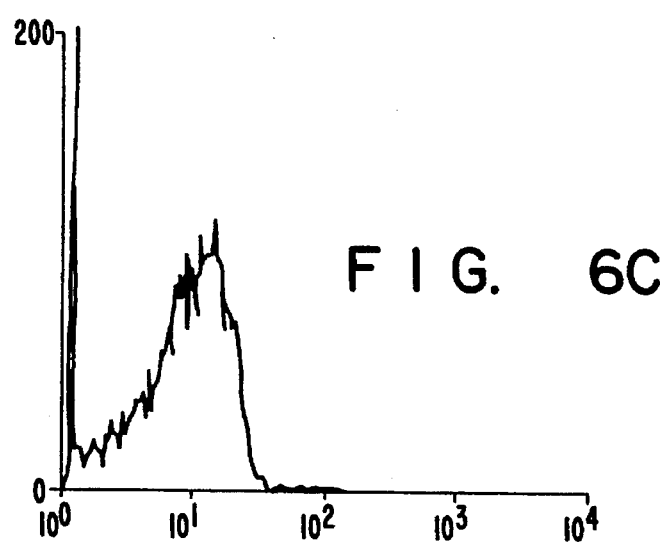

Anti-C5aR(9–29) was also assessed for the ability to bind to human peripheral blood-derived cells (FIGS. 6A, B and C). Unstimulated normal PMN were incubated with anti-C5aR(9–29) or RγG and subjected to single color flow cytometric analysis. Cells were stained with PE-conjugated 2° Ab [F(ab')2 fragments of anti-rabbit IgG] only protein A-purified anti-C5aR(9–29)+2° Ab or protein-A purified RγG+2° Ab. The results shown in FIGS. 6A, B and C indicated that staining with anti-C 5aR(9–29) (FIG. 6B) resulted in a greater MFI than with RγG (FIG. 6C).

In addition to PMN, macrophage and macrophage-like cell lines are known to express the C5aR. Unstimulated PBMC were assayed by dual color analysis to determine if cells expressing CD14 also bound the anti-C5aR(9–29). Forward and side scatter gates were set of measure the large granular cells, the population known to contain macrophage (FIGS. 7A, B and C). Cells were stained with PE-conjugated 2° Ab [F(ab')$_2$ fragments of anti-rabbit IgG] only protein A-purified RγG+2° Ab and FITC-conjugated anti-CD14 or protein-A purified anti-C 5aR(9–29)+2° Ab and FITC-conjugated anti-CD14. Gates were set to include the large granular cells only. The results in FIGS. 7A, B and C indicated that the majority of these gated cells were CD14+ (FIG. 7B). When these cells were also analyzed for their ability to bind anti-C5aR(9–29) a significant percentage of double positive (CD14$^+$,C5aR$^+$) cells were observed (FIG. 7C). In contrast, control staining (i.e., RγG) of these cells did not yield significant numbers of double positive cells. These results are consistent with anti-C5aR(9–29) interacting with the C5aR receptor on normal cells.

EXAMPLE 4

NEUTRALIZATION OF C5a-MEDIATED PMN CHEMOTAXIS BY ANTI-C5aR(9–29)

Figure 8:
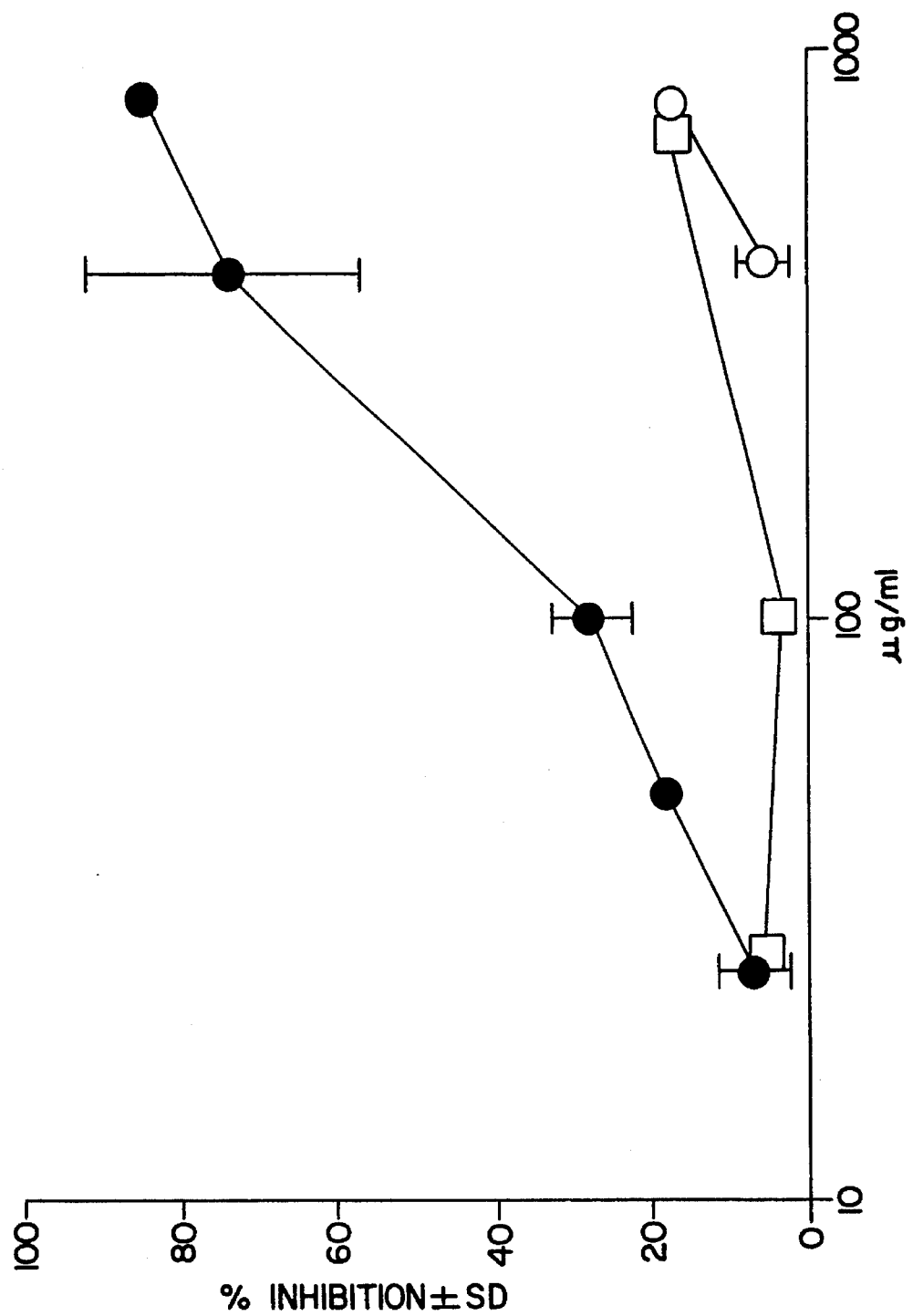
FIG. 8 shows the percent inhibition of human PMN chemotaxis to C5a by anti-C5aR (9–29).

A major proinflammatory activity associated with C5a is PMN chemotaxis. Local production of C5a in tissue spaces appears to result in increased vascular permeability, intravascular adherence of leukocytes, and establishment of a chemotactic concentration gradient for PMN. Results presented to this point indicate that anti-C5aR(9–29) antiserum binds to three different cells types expressing the human C5aR. To further explore Ab specificity, F(ab')2 fragments of anti-C5aR(9–29) and RγG were assayed for their ability to neutralize C5a-mediated PMN chemotactic activity. Preincubation of PMN with anti-C5aR(9–29) was found to inhibit PMN chemotaxis inducted by ZAS-activated serum in a dose dependent manner (FIG. 8). PMN were preincubated with buffer or various amount of F(ab')2 anti-C5aR(9–29) or RγG for 20 min and were then assessed for their ability to migrate in response to chemotactic stimulants (10% ZAS or $1\times10^{-8}$ M f-MLF) [anti-C5aR(9–29)+ZAS (●) and anti-C5aR(9–29)+f-MLF (□)] or RγG [RγG+ZAS (○)] (FIG. 8). Each data point represents the mean ± SD of 2–4 experiments performed with different blood donors. Anti-C5aR(9–29) was found to significantly reduce ($p<0.05$) ZAS-induced PMN chemotaxis.

C5a is known to be the major chemotactic mediator present in ZAS-activated serum. Maximal inhibition (≈80%) was achieved with 800 μg/ml of Ab. $ED_{50}$ suppression was achieved with approximately 100 μg/ml F(ab')2 anti-C5aR(9–29). Equivalent quantities of RγG did not induced significant inhibition of PMN chemotaxis. In contrast to C5a-mediated chemotaxis, F(ab')2 anti-C5aR(9–29) produced minimal inhibition (≦20%) of f-MLF-induced chemotaxis at 800 μg/ml. Taken together these results suggest that suppression of C5a-induced chemotaxis by anti-C5aR(9–29) is a specific event.

EXAMPLE 5

NEUTRALIZATION OF C5a-MEDIATED ENZYME RELEASE

BY ANTI-C5aR(9–29) Ab

Figure 9:
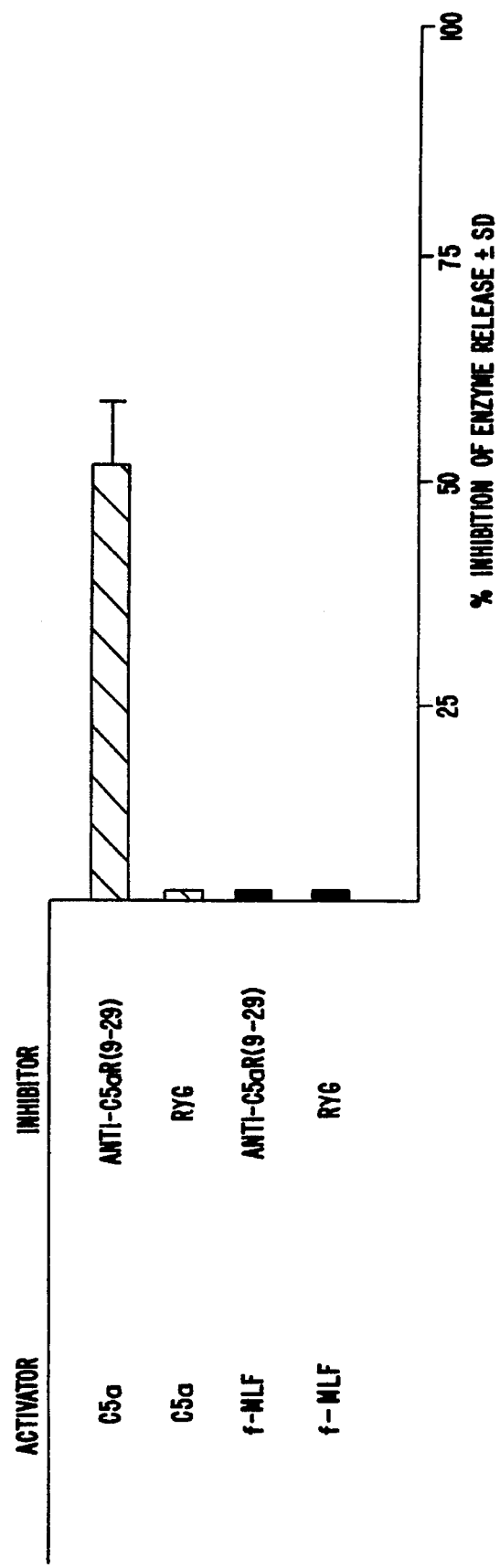
FIG. 9 shows the percent inhibition of C5a-induced enzyme release from human PMNs by anti-C5aR (9–29).

In addition to chemotaxis, another biologic activity associated with C5a is the induction of enzyme release from PMN (Ember, J. A., et al., *J. Immunol.*, 148:3165, 1992). To determine if the peptide-specific Ab could block enzyme release, PMN were preincubated with $F(ab')_2$ anti-C5aR(9–29) or RγG followed by the addition of stimulants (C5a or f-MLF) and the amount of β-G released into the culture supernatants was measured. Cells were preincubated with buffer or 400 μg/ml of F(ab')2 anti-C5aR(9–29) or RγG for 20 min at room temperature and were then assessed for their ability to release β-G in response to stimulation with human C5a ($1\times10^{-6}$M) or f-MLF ($1\times10^{-6}$ M). Each data point represents the mean ± SD of 2–4 experiments performed with different blood donors. Anti-C5aR(9–29) was found to significantly ($p<0.05$) reduce C5a-induced β-G release from PMN. Preincubation of PBMC with 400 μg/ml anti-C 5aR(9–29) suppressed C5a-mediated but not f-MLF-mediated enzyme release (FIG. 9). Inhibition of C5a-mediated enzyme release by anti-C5aR(9–29) was dependent upon the concentration of C5a used. Results from these experiments support data obtained in the chemotactic studies indicating that anti-C5aR(9–29) neutralizes C5aR-mediated proinflammatory activities.

EXAMPLE 6

NEUTRALIZATION OF C5a-MEDIATED CYTOKINE PRODUCTION

BY ANTI-C5aR(9–29)

A major component of the inflammatory and immunoregulatory properties of C5a appears to be activation of multiple cytokine cascades. Natural and recombinant human C5a directly or indirectly induce the production of IL-1, IL-6, IL-8, and TNF-α. F(ab')2 anti-C5aR(9–29) and RγG were assessed for an ability to inhibit natural C5a-mediated production of IL-6 and IL-8.

Human PBMC were preincubated with 200 μg/ml of F(ab')2 anti-C5aR(9–29) or RγG for 1.5 h at 37° C. (FIGS. 10A and B). Following the preincubation the cells were assessed for their ability to produce: FIG. 10A; IL-8 upon stimulation with either human C5a (0.1 μg/ml) or LPS (1.0 μg/ml). IL-8 levels in the culture supernatants were measured with an IL-8 specific ELISA. Data represent the mean and SD of two experiments with different PMBC donors. Specific values for IL-8 synthesis were: media control=38 ±5 ng/ml; C5a stimulation=255 ±5 ng/ml; and LPS stimulation=200 ±20 ng/ml. Anti-C5aR(9–29) was found to significantly ($p<0.05$) reduce IL-8 production from macrophages. FIG. 10B; IL-6 upon stimulation with either human C5a (0.1 μg/ml) or LPS (1.0 μg/ml). IL- 6 levels in the culture supernatants were measured with an IL-6 specific ELISA. Data represent the mean and SD of two experiments with different PMBC donors. Specific values for IU6 synthesis were: media control=≦1 ng/ml; C5a stimulation=12 ±3 ng/ml; and LPS stimulation=18±1 ng/ml. Anti-C 5aR(9–29) was found to significantly ($p<0.05$) reduce IL-6 production from macrophages.

Preincubation of PBMC with 200 μg/ml $F(ab')_2$ anti-C5aR peptide Ab resulted in a significant inhibition (65%) of IL-8 synthesis (FIG. 10A). Preincubation of companion cultures with equivalent quantities of Ab did not inhibit LPS-induced IL-8 synthesis. Moreover, preculture of PBMC with 200 μg of F(ab')2 RγG failed to block either C5a- or LPS-induced IL-8 production. In addition to IL-8 synthesis, culture supernatants were assayed for the presence of IL-6 by ELISA. Our results indicate that anti-C5aR(9–29) neutralized C5a-induced production of IL-6 (FIG. 10B). Furthermore, C5aR peptide specific antiserum was incapable of suppressing LPS-mediated IL-6 synthesis. Combined, the data from these experiments suggest that anti-C5aR(9–29) specifically inhibits the entire spectrum of C5a-mediated biologic activities.

EXAMPLE 7

GENERATION AND CHARACTERIZATION

OF MONOCLONAL ANTI-C5aR ANTIBODIES

Based on the results obtained with polyclonal rabbit-anti C5aR peptide antibodies, monoclonal antibodies were generated to C5aR peptides. Monoclonal antibodies were generated using standard techniques known in the art (Kohler and Milstein, supra). Briefly, mice were immunized as described in the rabbit and one mouse spleen was used for the fusion. After the fusion, 864 initial culture wells were plated. Of these 864 wells, supernatants from 22 wells contained antibodies that recognized the specific immunogen (i.e., C5aR (9–29)). Initial results indicated that one clone (6G4, IgM isotype) out of the 22 positive wells could bind to the native C5aR in the peptide specific ELISA. Ascities fluid from mice injected with 6G4 was screened for its ability to bind to C5aR(9–29) in the peptide specific ELISA.

Figure 11:
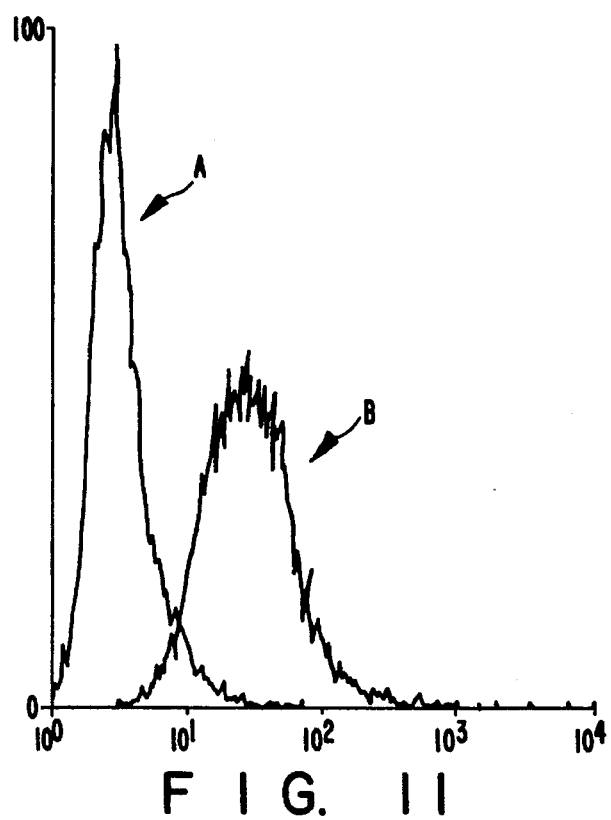
FIG. 11 shows a single color FACS analysis of U937 cells.

Monoclonal 6G4 was also tested for the ability to bind to U937 (a macrophage-like cell line) cells by single color flow cytometric analysis. The results indicated that 6G4 binds to U937 cells. In contrast supernatants from 3 other hybrid clones failed to bind to U937 cells. FIG. 11 shows cells that were stained with FITC-anti mouse IgM+IgG (peak A) or a combination of mAb 6G4+FITC-anti mouse IgM+IgG (peak B).

Figure 12:
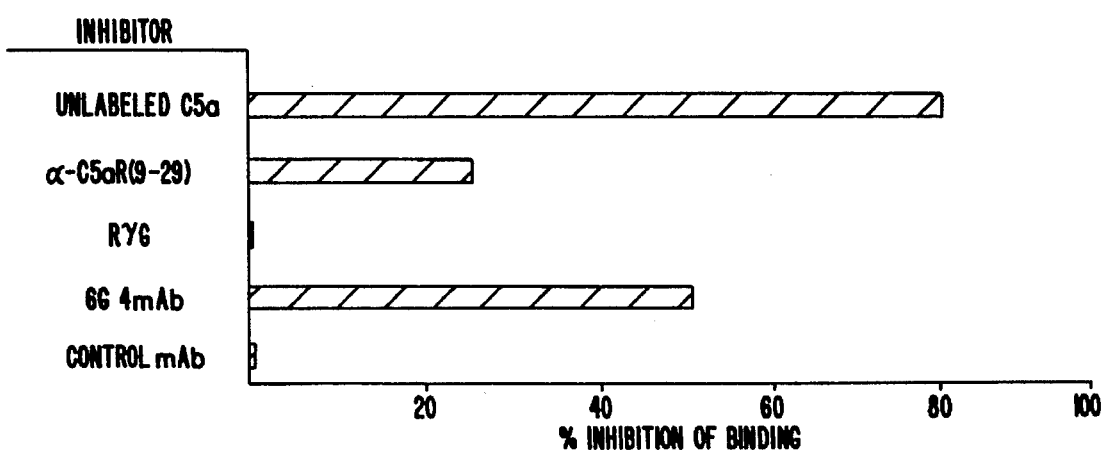
FIG. 12 shows inhibition of $^{125}$I-C5a binding to human PMN.
Figure 13:
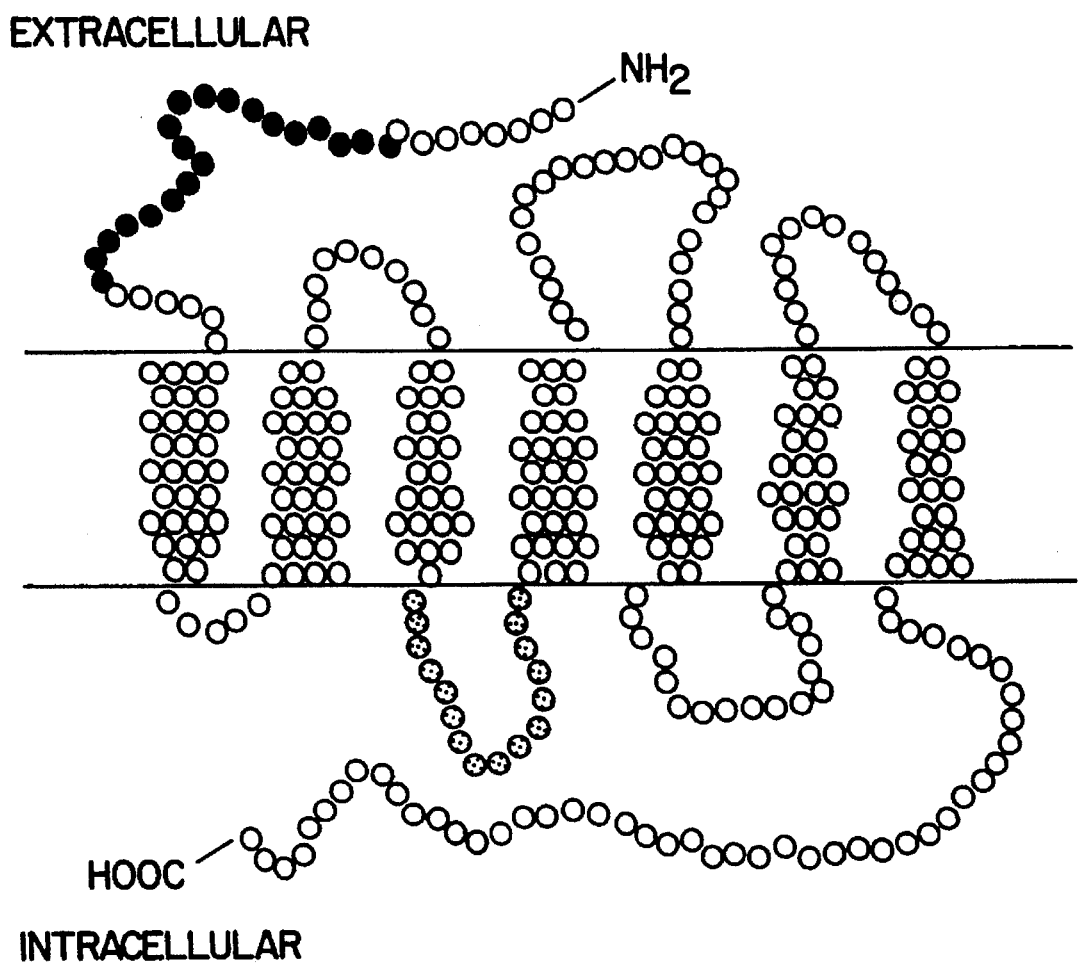
FIG. 13 shows a schematic model of the human C5aR. The residues in black represent C5aR (9–29) and the stippled residues represent C5aR (133–148).

These data suggest that the polyclonal Ab and mAb bind to cells expressing the human C5aR. To directly determine if these Abs compete with C5a for binding to C5aR, radiolabeled C5a binding studies were conducted (FIG. 12). Normal human PMN were incubated with $^{125}$I-C5a alone, $^{125}$I-C5a+100-fold excess unlabeled C5a, $^{125}$I-C5a+anti-C5aR(9–29), $^{125}$I-C5a+RGG, $^{125}$I-C 5a+ascites fluid containing mAb 6G4, or $^{125}$I-C5a+control ascites. Cells were incubated with $^{125}$-I-C5a (0.4 nM) for 1 h at 0° C. in the presence of different inhibitors. $^{125}$I-C5a binding inhibition was expressed as the reduction of uncompeted $^{125}$-I-C5a binding to the cells. The results presented in FIG. 12 indicate that both polyclonal and monoclonal anti-C5aR inhibit $^{125}$I-C5a binding to the C5aR. These results further confirm the specific of the anti-C 5aR immunoreagents.

The foregoing is meant to illustrate, but not to limit, the scope of the invention. Indeed, those of ordinary skill in the art can readily envision and produce further embodiments, based on the teachings herein, without undue experimentation.

SEQUENCE ID LISTING

Sequence ID No.1 is the amino acid sequence for amino acid residues 9–29 (amino terminus) of the: C5aR.

Sequence ID No.2 is the amino acid sequence for amino acid residues 133–148 of the C5aR.

Sequence ID No.s 3 and 4 are the nucleotide sequences of primers for human C5aR coding sequences.

We claim:

1. An antibody which binds to a peptide having the amino acid sequence of Sequence ID No. 1 and conservative variations thereof.

2. The antibody of claim 1, wherein the antibody is polyclonal.

3. The antibody of claim 1, wherein the antibody is monoclonal.

4. The antibody of claim 3 which has the specificity of the monoclonal antibody produced by cell line ATCC HB 11382.

5. The antibody of claim 4 which is produced by ATCC HB 11384.

* * * * *

UNITED STATES PATENT AND TRADEMARK OFFICE
CERTIFICATE OF CORRECTION

PATENT NO. : 5,480,974
DATED : January 2, 1996
INVENTOR(S) : Morgan, et al

It is certified that error appears in the above-identified patent and that said Letters Patent is hereby corrected as shown below:

At column 13, line 67, "cherootaxis" should read as —chemotaxis—;
at column 14, lines 38-39, "1x10⁻₆M" should read —1x10⁻⁶M—;
at column 14, lines 63-64, "5'-ACGAATTCTTACT-ACACTGCCTGGGTCTTC-3'" should read as —5'-ACGAATTCTTACTACACTGCCTGGGTCTTC-3'—;
at column 14, line 62, replace "SEQUENCE ID" with —sequence ID—;
at column 14, line 66, "349:61 4" should read as —349:614—;
at column 16, line 6, replace "sell" with –cell—;
at column 20, line 18, replace "IU6" with —IL-6—
at column 21, line 15, replace "specific" with —specificity—
at column 21, line 15, replace "anti–C 5aR" with —anti–C5aR—;

IN THE CLAIMS:
At column 24, line 34, replace "11382" with —11384—;

Signed and Sealed this

Twelfth Day of October, 1999

*Attest:*

Q. TODD DICKINSON

*Attesting Officer*   *Acting Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: C5aR(9-29)

( i x ) FEATURE:
        ( A ) NAME/KEY: Peptide
        ( B ) LOCATION: 1..21

( x i ) SEQUENCE DESCRIPTION: SEQ ID NO:1:

```
Pro Asp Tyr Gly His Tyr Asp Asp Lys Asp Thr Leu Asp Leu Asn Thr
 1               5                   10                  15
Pro Val Asp Lys Thr
                20
```

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: C5aR(133-148)

( i x ) FEATURE:
        ( A ) NAME/KEY: Peptide
        ( B ) LOCATION: 1..16

( x i ) SEQUENCE DESCRIPTION: SEQ ID NO:2:

```
Arg Phe Leu Leu Val Glu Phe Lys Pro Ile Trp Cys Gln Asn Phe Arg
 1               5                   10                  15
```

( 2 ) INFORMATION FOR SEQ ID NO:3:

( i ) SEQUENCE CHARACTERISTICS:

(A) LENGTH: 35 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..35

(xi) SEQUENCE DESCRIPTION: SEQ ID NO:3:

TAGAATTCCC AGCCATGAAC TCCTTCAATT ATACC    35

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..30

(xi) SEQUENCE DESCRIPTION: SEQ ID NO:4:

ACGAATTCTT ACTACACTGC CTGGGTCTTC    30